United States Patent
DeVries et al.

(10) Patent No.: US 8,118,024 B2
(45) Date of Patent: Feb. 21, 2012

(54) MECHANICAL VENTILATION SYSTEM UTILIZING BIAS VALVE

(75) Inventors: Douglas F. DeVries, Kenmore, WA (US); Todd Allum, Redlands, CA (US)

(73) Assignee: CareFusion 203, Inc., San Diego, CA (US)

( * ) Notice: Subject to any disclaimer, the term of this patent is extended or adjusted under 35 U.S.C. 154(b) by 422 days.

(21) Appl. No.: 11/486,346

(22) Filed: Jul. 13, 2006

(65) Prior Publication Data

US 2006/0249153 A1    Nov. 9, 2006

Related U.S. Application Data

(63) Continuation-in-part of application No. 10/912,747, filed on Aug. 4, 2004, now Pat. No. 7,188,621.

(60) Provisional application No. 60/492,421, filed on Aug. 4, 2003.

(51) Int. Cl.
*A61M 16/00* (2006.01)
*A62B 9/02* (2006.01)

(52) U.S. Cl. ......... 128/204.21; 128/200.24; 128/204.18; 128/205.24

(58) Field of Classification Search ............. 128/200.24, 128/204.18, 204.21, 204.23, 205.24; 137/538, 137/543.19, 529, 534, 522, 523; 251/65, 251/83

See application file for complete search history.

(56) References Cited

U.S. PATENT DOCUMENTS

| | | | |
|---|---|---|---|
| 56,611 A | 7/1866 | Roots | |
| 56,614 A | 7/1866 | Roots | |
| 587,907 A | 8/1897 | Ames et al. | |
| 1,769,153 A | 7/1930 | Meyer | |
| 2,014,932 A | 9/1935 | Hallett | |
| 2,787,999 A | 4/1957 | Bennett | |
| 3,089,638 A | 5/1963 | Rose | |
| 3,094,274 A | 6/1963 | Thompson | |
| 3,371,856 A | 3/1968 | Thelen et al. | |
| 3,459,395 A | 8/1969 | Scotto | 248/20 |
| 3,658,443 A | 4/1972 | Fumagalli | |
| 3,865,523 A | 2/1975 | Baehr | |
| 3,916,888 A * | 11/1975 | Buck et al. | 128/204.21 |

(Continued)

FOREIGN PATENT DOCUMENTS

DE    3238015    4/1984

(Continued)

OTHER PUBLICATIONS

Eaton, "Why an Eaton Charger?", www.eaton.com/supercharger/whysuper.html.

(Continued)

*Primary Examiner* — Annette Dixon

(57) ABSTRACT

A portable mechanical ventilator having a ROOTS® blower is configured to provide a desired gas flow and pressure to a patient circuit. The mechanical ventilator includes a flow meter operative to measure gas flow produced by the ROOTS® blower and an exhalation control module configured to operate an exhalation valve connected to the patient circuit. A bias valve connected between the ROOTS® blower and the patient circuit is specifically configured to generate a bias pressure relative to the patient circuit pressure at the exhalation control module. The bias valve is further configured to attenuate pulsating gas flow produced by the ROOTS® blower such that gas flowing to the mass flow meter exhibits a substantially constant pressure characteristic. The bias pressure facilitates closing of the exhalation valve at the start of inspiration, regulates positive end expiratory pressure during exhalation, and purges sense lines via a pressure transducer module.

10 Claims, 3 Drawing Sheets

U.S. PATENT DOCUMENTS

| | | | |
|---|---|---|---|
| 3,941,206 A | 3/1976 | Halter | 181/50 |
| 4,080,103 A | 3/1978 | Bird | |
| 4,121,578 A | 10/1978 | Torzala | 128/142 R |
| 4,215,977 A | 8/1980 | Weatherston | |
| 4,220,219 A | 9/1980 | Flugger | |
| 4,227,869 A | 10/1980 | Eriksson | |
| 4,239,039 A | 12/1980 | Thompson | 128/205.24 |
| 4,248,194 A | 2/1981 | Drutchas et al. | |
| 4,267,899 A | 5/1981 | Wagner et al. | 181/272 |
| 4,323,064 A | 4/1982 | Hoenig et al. | 128/204.21 |
| 4,448,192 A | 5/1984 | Stawitcke et al. | 128/204.26 |
| 4,455,132 A | 6/1984 | Messori | |
| 4,495,947 A | 1/1985 | Motycka | |
| 4,564,345 A | 1/1986 | Mueller | |
| 4,595,349 A | 6/1986 | Preston et al. | |
| 4,609,335 A | 9/1986 | Uthoff, Jr. | |
| 4,637,439 A * | 1/1987 | Jeans | 141/18 |
| 4,656,553 A | 4/1987 | Brown | |
| 4,666,384 A | 5/1987 | Kaga et al. | |
| 4,673,058 A | 6/1987 | Roberts et al. | |
| 4,684,330 A | 8/1987 | Andersson et al. | |
| 4,686,999 A | 8/1987 | Snyder et al. | 128/716 |
| 4,702,240 A | 10/1987 | Choui | |
| 4,747,403 A * | 5/1988 | Gluck et al. | 128/204.21 |
| 4,768,934 A | 9/1988 | Soeters, Jr. | |
| 4,781,541 A | 11/1988 | Sohler et al. | |
| 4,794,922 A | 1/1989 | DeVries | |
| 4,838,257 A * | 6/1989 | Hatch | 128/204.18 |
| 4,844,044 A | 7/1989 | McGovern | |
| 4,846,302 A | 7/1989 | Hetherington | |
| 4,867,151 A | 9/1989 | Bird | |
| 4,897,583 A | 1/1990 | Rees | |
| 4,905,685 A | 3/1990 | Olsson et al. | |
| 4,938,670 A | 7/1990 | Lee | |
| 4,957,107 A * | 9/1990 | Sipin | 128/204.21 |
| 4,975,032 A | 12/1990 | Arai et al. | |
| 5,040,959 A | 8/1991 | Fukagawa | |
| 5,056,995 A | 10/1991 | Tamura et al. | 418/201.1 |
| 5,127,400 A * | 7/1992 | DeVries et al. | 128/205.24 |
| 5,131,829 A | 7/1992 | Hampton | |
| 5,145,349 A | 9/1992 | McBurnett | 418/206 |
| 5,152,684 A | 10/1992 | Steffens | |
| 5,161,525 A | 11/1992 | Kimm et al. | 128/204.26 |
| 5,211,170 A | 5/1993 | Press | 128/204.18 |
| 5,222,148 A | 6/1993 | Yuan | 381/71 |
| 5,237,987 A | 8/1993 | Anderson et al. | 128/204.18 |
| 5,239,994 A | 8/1993 | Atkins | 128/204.18 |
| 5,253,486 A | 10/1993 | Sugahara et al. | |
| 5,335,651 A | 8/1994 | Foster et al. | 128/202.13 |
| 5,350,888 A | 9/1994 | Sager, Jr. et al. | |
| 5,384,527 A | 1/1995 | Rozman et al. | |
| 5,388,575 A | 2/1995 | Taube | |
| 5,398,676 A | 3/1995 | Press et al. | 128/204.23 |
| 5,428,276 A | 6/1995 | Carobolante et al. | |
| 5,430,362 A | 7/1995 | Carr et al. | |
| 5,439,358 A * | 8/1995 | Weinbrecht | 418/15 |
| 5,452,714 A | 9/1995 | Anderson et al. | 128/205.11 |
| 5,461,293 A | 10/1995 | Rozman et al. | |
| 5,493,200 A | 2/1996 | Rozman et al. | |
| 5,493,892 A * | 2/1996 | Sherman | 73/1.42 |
| 5,495,162 A | 2/1996 | Rozman et al. | |
| 5,495,163 A | 2/1996 | Rozman et al. | |
| 5,542,416 A | 8/1996 | Chalvignac | |
| 5,577,152 A | 11/1996 | Chen | 388/804 |
| 5,582,163 A | 12/1996 | Bonassa | 128/204.26 |
| 5,632,270 A | 5/1997 | O'Mahony et al. | 128/204.24 |
| 5,638,600 A | 6/1997 | Rao et al. | |
| 5,664,563 A | 9/1997 | Schroeder et al. | 128/204.25 |
| 5,687,717 A | 11/1997 | Halpern et al. | 128/630 |
| 5,694,926 A | 12/1997 | DeVries et al. | |
| 5,701,883 A | 12/1997 | Hete et al. | 128/204.26 |
| 5,702,240 A | 12/1997 | O'Neal et al. | |
| 5,720,276 A * | 2/1998 | Kobatake et al. | 128/204.18 |
| 5,760,348 A | 6/1998 | Heuser | 181/272 |
| 5,763,792 A | 6/1998 | Kullik | 73/861.53 |
| 5,783,782 A | 7/1998 | Sterrett et al. | |
| 5,799,652 A | 9/1998 | Kotliar | |
| 5,823,186 A * | 10/1998 | Rossen et al. | 128/204.21 |
| 5,831,223 A | 11/1998 | Kesselring | |
| 5,868,133 A | 2/1999 | DeVries et al. | |
| 5,871,465 A | 2/1999 | Vasko | |
| 5,880,586 A | 3/1999 | Dukart et al. | |
| 5,881,722 A | 3/1999 | DeVries et al. | |
| 5,918,597 A | 7/1999 | Jones et al. | |
| 5,931,159 A * | 8/1999 | Suzuki et al. | 128/204.18 |
| 5,934,274 A | 8/1999 | Merrick et al. | |
| 5,944,501 A | 8/1999 | Yokoi | |
| 5,996,731 A | 12/1999 | Czabala et al. | |
| 6,009,871 A | 1/2000 | Kiske et al. | 128/204.21 |
| 6,065,944 A | 5/2000 | Cobb | |
| 6,070,576 A | 6/2000 | Banucci et al. | |
| 6,076,523 A | 6/2000 | Jones et al. | 128/205.11 |
| 6,099,277 A | 8/2000 | Patel et al. | |
| 6,102,038 A | 8/2000 | DeVries | |
| 6,125,844 A | 10/2000 | Samiotes | 128/200.23 |
| 6,152,129 A | 11/2000 | Jones | |
| 6,152,135 A | 11/2000 | DeVries et al. | |
| 6,155,257 A | 12/2000 | Lurie et al. | 128/204.23 |
| 6,158,430 A | 12/2000 | Pfieffer et al. | 128/202.27 |
| 6,158,434 A | 12/2000 | Lugtigheid et al. | 128/204.22 |
| 6,164,412 A | 12/2000 | Allman | |
| 6,176,693 B1 | 1/2001 | Conti | 418/180 |
| 6,237,592 B1 | 5/2001 | Surjadi et al. | |
| 6,239,564 B1 | 5/2001 | Boe et al. | |
| 6,247,906 B1 | 6/2001 | Pijanowski | |
| 6,279,574 B1 | 8/2001 | Richardson et al. | 128/204.18 |
| 6,279,576 B1 | 8/2001 | Lambert | |
| 6,283,246 B1 | 9/2001 | Nishikawa | 181/255 |
| 6,305,372 B1 | 10/2001 | Servidio | 128/204.21 |
| 6,349,724 B1 | 2/2002 | Burton et al. | |
| 6,354,558 B1 | 3/2002 | Li | 248/615 |
| 6,412,483 B1 | 7/2002 | Jones et al. | 128/205.11 |
| 6,468,222 B1 | 10/2002 | Mault et al. | |
| 6,474,960 B1 | 11/2002 | Hansmann | |
| 6,479,987 B1 | 11/2002 | Marx et al. | |
| 6,484,719 B1 | 11/2002 | Jones | |
| 6,526,970 B2 | 3/2003 | DeVries et al. | |
| 6,543,449 B1 | 4/2003 | Woodring et al. | |
| 6,558,137 B2 | 5/2003 | Tomell et al. | 417/312 |
| 6,564,798 B1 | 5/2003 | Jalde | 128/205.24 |
| 6,571,792 B1 | 6/2003 | Hendrickson et al. | 128/203.12 |
| 6,571,796 B2 | 6/2003 | Banner et al. | 128/204.26 |
| 6,591,835 B1 | 7/2003 | Blanch | 128/204.25 |
| 6,615,446 B2 | 9/2003 | Noreen et al. | |
| 6,615,831 B1 | 9/2003 | Tuitt et al. | 128/204.18 |
| 6,619,286 B2 | 9/2003 | Patel | 128/204.26 |
| 6,619,325 B2 * | 9/2003 | Gray, Jr. | 138/30 |
| 6,626,175 B2 | 9/2003 | Jafari et al. | 128/204.21 |
| 6,629,525 B2 | 10/2003 | Hill et al. | 128/202.26 |
| 6,629,531 B2 | 10/2003 | Gleason et al. | 128/205.25 |
| 6,629,934 B2 | 10/2003 | Mault et al. | 600/538 |
| 6,631,716 B1 | 10/2003 | Robinson et al. | 128/204.21 |
| 6,637,430 B1 | 10/2003 | Voges et al. | 128/200.14 |
| 6,651,658 B1 | 11/2003 | Hill et al. | |
| 6,666,209 B2 | 12/2003 | Bennett et al. | 128/200.24 |
| 6,672,300 B1 | 1/2004 | Grant | 124/204.26 |
| 6,691,702 B2 | 2/2004 | Appel et al. | |
| 6,691,707 B1 | 2/2004 | Gunaratnam et al. | 128/206.21 |
| 6,708,690 B1 | 3/2004 | Hete et al. | |
| 6,745,770 B2 | 6/2004 | McAuliffe et al. | 128/205.24 |
| 6,752,240 B1 | 6/2004 | Schlagenhaft | 181/249 |
| 6,764,534 B2 | 7/2004 | McCombs et al. | 96/111 |
| 6,770,037 B2 | 8/2004 | Sullivan et al. | 600/529 |
| 6,782,888 B1 | 8/2004 | Friberg et al. | 128/204.18 |
| 6,802,225 B2 | 10/2004 | Shahar et al. | 73/861.52 |
| 6,820,618 B2 | 11/2004 | Banner et al. | 128/204.23 |
| 6,837,239 B2 * | 1/2005 | Beizndtsson et al. | 128/201.25 |
| 6,837,260 B1 | 1/2005 | Kuehn | 137/315.01 |
| 6,877,511 B2 | 4/2005 | DeVries et al. | |
| 6,907,373 B2 | 6/2005 | Walter et al. | |
| 6,968,842 B1 | 11/2005 | Truschel et al. | 128/204.18 |
| 6,979,181 B1 | 12/2005 | Kidd | |
| 7,004,908 B2 | 2/2006 | Sullivan et al. | 600/529 |
| 7,011,092 B2 | 3/2006 | McCombs et al. | 128/205.12 |
| 7,032,589 B2 | 4/2006 | Kerechanin et al. | 128/200.24 |
| 7,063,084 B2 | 6/2006 | McDonald | 128/200.28 |
| 7,066,178 B2 | 6/2006 | Gunaratnam et al. | 128/206.21 |

| | | | | | | |
|---|---|---|---|---|---|---|
| 7,066,985 B2 | 6/2006 | Deane et al. ................... 95/96 | | 2007/0062532 A1 | 3/2007 | Choncholas ............. 128/204.23 |
| 7,073,499 B1 | 7/2006 | Reinhold et al. ......... 128/200.18 | | 2007/0068526 A1 | 3/2007 | Lang et al. ............... 128/204.22 |
| 7,086,366 B1 | 8/2006 | Killion ...................... 123/192.2 | | 2007/0079826 A1 | 4/2007 | Kramer et al. ........... 128/200.14 |
| 7,118,536 B2 | 10/2006 | Haberland et al. ............ 600/538 | | 2007/0113843 A1 | 5/2007 | Hughes .................... 128/200.24 |
| 7,121,276 B2 | 10/2006 | Jagger et al. ............. 128/201.21 | | 2007/0113849 A1 | 5/2007 | Matthews et al. ........ 128/204.22 |
| 7,168,429 B2 | 1/2007 | Matthews et al. ........ 128/204.21 | | 2007/0169776 A1 | 7/2007 | Kepler et al. ............ 128/200.23 |
| 7,171,963 B2 | 2/2007 | Jagger et al. ............. 128/201.21 | | 2007/0181127 A1 | 8/2007 | Jin et al. ................... 128/204.21 |
| 7,183,681 B2 | 2/2007 | Segawa et al. ............. 310/68 B | | 2007/0193580 A1 | 8/2007 | Feldhahn et al. ........ 128/204.18 |
| 7,188,621 B2 | 3/2007 | DeVries et al. .......... 128/204.21 | | 2007/0215146 A1 | 9/2007 | Douglas et al. .......... 128/200.24 |
| 7,225,809 B1 | 6/2007 | Bowen et al. ............ 128/204.21 | | 2007/0221224 A1 | 9/2007 | Pittman et al. ........... 128/204.22 |
| 7,226,280 B1 | 6/2007 | Yokoi ........................ 418/206.4 | | 2007/0235030 A1 | 10/2007 | Teetzel et al. ............ 128/205.12 |
| 7,329,304 B2 | 2/2008 | Bliss et al. ....................... 95/12 | | 2007/0265877 A1 | 11/2007 | Rice et al. ........................ 705/2 |
| 7,331,342 B2 | 2/2008 | Spearman et al. ........ 128/203.14 | | 2007/0277825 A1 | 12/2007 | Bordewick et al. ...... 128/204.23 |
| 7,335,243 B2 | 2/2008 | Homan et al. ................ 55/385.2 | | 2008/0000474 A1 | 1/2008 | Jochle et al. ............. 128/204.18 |
| 7,351,034 B2 | 4/2008 | Cens et al. ...................... 416/61 | | 2008/0029096 A1 | 2/2008 | Kollmeyer et al. ...... 128/204.21 |
| 7,368,005 B2 | 5/2008 | Bliss et al. ...................... 96/121 | | 2008/0035149 A1 | 2/2008 | Sutton ...................... 128/205.24 |
| 2001/0044588 A1 | 11/2001 | Mault ........................... 600/549 | | 2008/0039701 A1 | 2/2008 | Ali et al. ...................... 600/301 |
| 2002/0134378 A1 | 9/2002 | Finnegan et al. ......... 128/200.24 | | 2008/0051674 A1 | 2/2008 | Davenport et al. |
| 2003/0057904 A1 | 3/2003 | Sacher ........................... 318/268 | | 2008/0066739 A1 | 3/2008 | LeMahieu et al. ........ 128/200.14 |
| 2003/0208113 A1 | 11/2003 | Mault et al. ................... 600/316 | | 2008/0078395 A1 | 4/2008 | Ho et al. .................. 128/205.24 |
| 2004/0015364 A1 | 1/2004 | Sulc | | 2008/0099017 A1 | 5/2008 | Bordewick et al. ...... 128/204.21 |
| 2004/0061996 A1 | 4/2004 | Kamphuis et al. | | 2008/0110455 A1 | 5/2008 | Dunsmore et al. ....... 128/200.24 |
| 2004/0074495 A1 | 4/2004 | Wickham et al. ........ 128/204.18 | | 2008/0110458 A1 | 5/2008 | Srinivasan et al. ........ 128/203.26 |
| 2004/0147818 A1 | 7/2004 | Levy et al. ..................... 600/300 | | 2008/0110462 A1 | 5/2008 | Chekal et al. ............ 128/204.26 |
| 2004/0190236 A1 | 9/2004 | Medica et al. | | 2008/0127976 A1 | 6/2008 | Acker et al. ............. 128/204.18 |
| 2004/0211422 A1 | 10/2004 | Arcilla et al. ............ 128/204.19 | | | | |
| 2004/0221854 A1 | 11/2004 | Hete et al. ................ 128/207.16 | | | | |
| 2004/0226562 A1 | 11/2004 | Bordewick ............... 128/204.23 | | | | |
| 2005/0051168 A1 | 3/2005 | DeVries et al. | | | | |
| 2005/0112013 A1 | 5/2005 | DeVries et al. ............. 418/206.1 | | | | |
| 2005/0124866 A1 | 6/2005 | Elaz et al. ..................... 600/301 | | | | |
| 2005/0166921 A1 | 8/2005 | DeVries et al. .......... 128/204.21 | | | | |
| 2005/0183902 A1 | 8/2005 | Segawa et al. | | | | |
| 2005/0188991 A1 | 9/2005 | Sun et al. ................. 128/204.23 | | | | |
| 2005/0241642 A1 | 11/2005 | Krzysztofik ............. 128/206.15 | | | | |
| 2006/0065672 A1 | 3/2006 | LeCourt et al. .................... 222/3 | | | | |
| 2006/0069326 A1 | 3/2006 | Heath .............................. 601/41 | | | | |
| 2006/0070624 A1 | 4/2006 | Kane et al. ............... 128/204.23 | | | | |
| 2006/0124128 A1 | 6/2006 | Deane et al. .............. 128/204.21 | | | | |
| 2006/0144396 A1 | 7/2006 | DeVries et al. ........... 128/204.21 | | | | |
| 2006/0144399 A1 | 7/2006 | Davidowski et al. .... 128/205.21 | | | | |
| 2006/0144405 A1 | 7/2006 | Gunaratnam et al. ... 128/206.21 | | | | |
| 2006/0150973 A1 | 7/2006 | Chalvignac .............. 128/214.21 | | | | |
| 2006/0174871 A1 | 8/2006 | Jagger et al. ............. 128/201.21 | | | | |
| 2006/0174872 A1 | 8/2006 | Jagger et al. ............. 128/201.21 | | | | |
| 2006/0174874 A1 | 8/2006 | Jagger et al. ............. 128/201.21 | | | | |
| 2006/0174875 A1 | 8/2006 | Jagger et al. ............. 128/201.21 | | | | |
| 2006/0174877 A1 | 8/2006 | Jagger et al. ............. 128/201.21 | | | | |
| 2006/0174878 A1 | 8/2006 | Jagger et al. ............. 128/201.21 | | | | |
| 2006/0174880 A1 | 8/2006 | Jagger et al. ............. 128/201.25 | | | | |
| 2006/0174881 A1 | 8/2006 | Jagger et al. ............. 128/201.25 | | | | |
| 2006/0174882 A1 | 8/2006 | Jagger et al. ............. 128/201.25 | | | | |
| 2006/0201503 A1 | 9/2006 | Breen ........................ 128/204.18 | | | | |
| 2006/0213518 A1 | 9/2006 | DeVries et al. ........... 128/204.21 | | | | |
| 2006/0249149 A1 | 11/2006 | Meier et al. .............. 128/204.18 | | | | |
| 2006/0266355 A1 | 11/2006 | Misholi ..................... 128/204.23 | | | | |
| 2006/0283450 A1 | 12/2006 | Shissler et al. ........... 128/204.21 | | | | |
| 2007/0044799 A1 | 3/2007 | Hete et al. ................ 128/205.11 | | | | |
| 2007/0062529 A1 | 3/2007 | Choncholas et al. .... 128/204.22 | | | | |

FOREIGN PATENT DOCUMENTS

| | | |
|---|---|---|
| DE | 3414064 | 10/1985 |
| DE | 3620792 | 12/1987 |
| DE | 19817356 | 10/1999 |
| EP | 0239026 | 9/1987 |
| EP | 0521709 | 1/1993 |
| EP | 0938909 | 9/1999 |
| EP | 1130761 | 9/2001 |
| EP | 1243282 | 9/2002 |
| FR | 2875891 | 9/2004 |
| FR | 20040452189 | 3/2006 |
| GB | 2157370 | 10/1985 |
| JP | 2001050774 | 2/2001 |
| JP | 2003124986 | 4/2003 |
| WO | WO 89/10768 | 11/1989 |
| WO | WO 92/11054 | 7/1992 |
| WO | WO 96/11717 | 4/1996 |
| WO | WO 97/11522 | 3/1997 |
| WO | WO 97/15343 | 5/1997 |
| WO | WO 99/64825 | 12/1999 |
| WO | WO 00/45883 | 8/2000 |
| WO | WO 02/11861 | 2/2002 |
| WO | WO 2004/040745 | 5/2004 |

OTHER PUBLICATIONS

M.L. Munjal, "Acoustics of Ducts and Mufflers," John Wiley & Sons, 1987, chapter 8.

Hinrichs, Dr. Gustavus "Introduction to General Chemistry, a Graded Course of One Hundred Lectures", *St. Louis, Mo: Hinrichs*, (1897), 87-89.

* cited by examiner

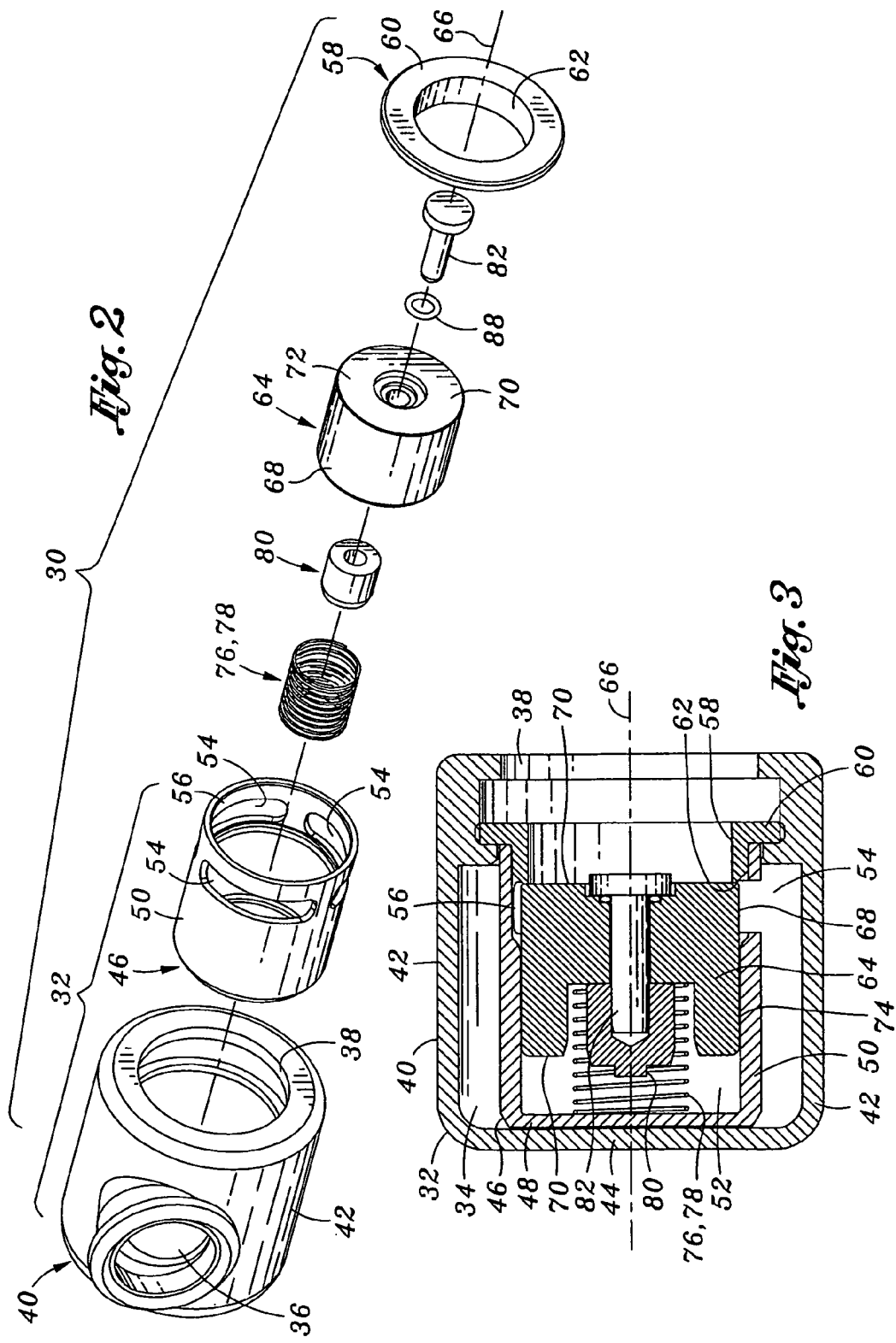

MECHANICAL VENTILATION SYSTEM UTILIZING BIAS VALVE

CROSS REFERENCE TO RELATED APPLICATIONS

This application is a continuation-in-part of U.S. patent application Ser. No. 10/912,747 filed Aug. 4, 2004 now U.S. Pat. No. 7,188,621, and claims the benefit of priority from U.S. Provisional Patent Application No. 60/492,421 filed Aug. 4, 2003, U.S. patent application Ser. No. 10/847,693 filed May 18, 2004, U.S. patent application Ser. No. 10/912,747 filed Aug. 4, 2004, U.S. patent application Ser. No. 10/985,528 filed Nov. 10, 2004, U.S. patent application Ser. No. 11/088,316 filed Mar. 23, 2005, and U.S. patent application Ser. No. 11/234,636 filed Sep. 23, 2005, the specifications and figures of all of which are expressly incorporated by reference herein.

STATEMENT RE: FEDERALLY SPONSORED RESEARCH/DEVELOPMENT

Not Applicable

BACKGROUND OF THE INVENTION

The present invention relates generally to mechanical ventilators and, more particularly, to a portable ventilator that incorporates a low-inertia, high speed, high efficiency ROOTS®-type blower that is specifically adapted to provide full ventilator functionality and which approximates the size of a small laptop computer while providing hours of battery-powered, full-service breathing assistance to a patient.

The prior art includes a wide variety of mechanical ventilators for patients requiring breathing assistance. Unfortunately, such mechanical ventilators have traditionally been configured as relatively large devices which occupy a relatively large volume of the limited space available in operating rooms and patient recovery rooms. In addition, such prior art mechanical ventilators are typically of low efficiency such that relatively large amounts of power are required in order to operate the device. In addition, mechanical ventilators of the prior art have not been truly portable devices in that such devices must typically be continuously connected to a main power supply during operation. The relatively large weight and bulk of such devices further limits their portability.

Advances in compressor technology as applied to mechanical ventilators have, to some degree, reduced the size and overall power consumption of mechanical ventilators. For example, U.S. Pat. No. 6,152,135 issued to DeVries et al. incorporates improvements in such compressor technology and, more specifically, provides a reduction in size and power to realize a truly self-contained and portable mechanical ventilator. Ventilators similar to the DeVries device may further include or are connectable to battery packs such that the mechanical ventilator may be mounted on a moveable stand in order to facilitate patient transport for limited durations without the constraints of connection to a stationary power source such as an electrical wall outlet.

In addition, mechanical ventilators similar to the DeVries device have realized improved functionality regarding their ability to deliver a variety of breath modes to the patient by using rotary drag compressors which operate under low pressure for delivery of breath to the patient. Such drag compressors may be operated in either variable speed or constant speed mode. Mechanical ventilators operating in variable speed mode provide inspiratory support (i.e., inhalation assistance) to a patient by rapidly accelerating the compressor from a standstill followed by rapid deceleration during the expiratory (i.e., exhalation) phase of the breathing cycle. Unfortunately, such rapid acceleration and deceleration necessitates complex drive circuitry for the compressor and consumption of high electrical currents. The relatively high current draw of such variable speed drag compressors increases the overall cost of the mechanical ventilator. Furthermore, the high current requirement necessitates the incorporation of bulky and heavy batteries for providing standby battery power as an emergency back-up when the ventilator is not connected to a stationary power source.

Alternatively, rotary drag compressors may be operated in constant speed mode in order to eliminate the limitations imposed by high current requirements of variable speed compressors. Unfortunately, such constant speed drag compressors possess their own set of inherent deficiencies which detract from the overall utility of the mechanical ventilator. For example, because the compressor runs at a constant speed, power is continuously consumed even during the expiratory phase (i.e. exhalation) when air or gas is not supplied to the patient. Although the power consumption may be reduced by recirculating the air flow during exhalation to an intake of the compressor, a considerable amount of standby battery power is still required to operate the mechanical ventilator when not connected to a stationary power source.

As can be seen, there exists a need in the art for a mechanical ventilator that is of small size and low weight in order to enhance its portability. Furthermore, there exists a need in the art for a portable mechanical ventilator that can provide breathing assistance to a patient for extended durations without the constraints of a stationary power source. In addition, there exists a need in the art for a portable mechanical ventilator that provides breathing assistance in volume and pressure control modes and which can be safely and quietly operated in the noise-sensitive environments of operating rooms, intensive care units and patient recovery rooms.

BRIEF SUMMARY OF THE INVENTION

The present invention is specifically adapted to address the above-mentioned deficiencies associated with mechanical ventilators for providing breathing assistance to a patient. More specifically, the present invention provides a portable mechanical ventilator incorporating a ROOTS® blower which allows for improved efficiency and reduced size and weight as compared to conventional mechanical ventilators. In addition, the small size and power efficiency of the mechanical ventilator provides mobility to patients who require continuous breathing assistance such as during patient transfer.

Advantageously, the mechanical ventilator includes a bias valve located downstream of the ROOTS® blower between a flow meter and a patient circuit. The bias valve is specifically adapted to attenuate or dampen the pulsating gas flow produced by the ROOTS® blower located upstream of the bias valve. Although the bias valve is located downstream of the ROOTS® blower, its dampening effect is transmitted back upstream due to confinement of the gas flow within the air column (i.e., between the ROOTS® blower outlet and the bias valve). The flow meter located downstream of the ROOTS® blower therefore receives dampened gas flow such that accurate gas flow measurements may be taken. A mechanical ventilator of the type incorporating a ROOTS® blower is described in detail in U.S. Patent Publication No. 2005/

0051168 entitled PORTABLE VENTILATOR SYSTEM to DeVries et al., the entire contents of which is expressly incorporated by reference herein.

In addition to dampening the pulsating flow output from the ROOTS® blower, the bias valve is also adapted to generate a bias pressure or elevated pressure relative to the patient circuit pressure. The bias valve may be comprised of a poppet that is engageable to a valve seat and which further includes a biasing member that is specifically configured to bias the poppet against the valve seat to create the desired amount of bias pressure. The bias pressure may be used by an exhalation control module in order to facilitate the closing of an exhalation valve at the start of inspiration. The exhalation valve may also regulate positive and expiratory pressure (PEEP) during exhalation and performs other functions.

The bias pressure also aids in the control of user-activated maneuvers such as inspiratory-hold, expiratory-hold and regulation of mean inspiratory pressure/negative inspiratory force (MIP/NIF). The bias pressure facilitates closing of the exhalation valve in order to prevent airflow into or out of the patient circuit during the performance of such user-activated maneuvers in a manner described in greater detail below. Ideally, the biasing member is configured to have a predetermined spring constant that is sufficient to bias the poppet against the valve seat such that the bias pressure is substantially constant across a flow range of the ROOTS® blower.

The ability to keep the bias pressure constant and relatively low across the flow range of the ROOTS® blower advantageously minimizes power consumption of the mechanical ventilator. In this regard, the biasing member preferably has a low spring constant which, combined with the free poppet travel, provides the preferred constant pressure characteristic over the flow range of the ROOTS® blower. The amount of exposed area of the poppet at the valve seat in combination with the spring preload defines the magnitude of the resistance against the pulsating gas flow produced by the ROOTS® blower which, in turn, results in generation of the desired amount of bias pressure.

In addition to generating a bias pressure, the bias valve is also configured to provide attenuation or dampening of the pulsating gas flow produced by the ROOTS® blower. As was earlier mentioned, measurement of the flow output of the ROOTS® blower is provided by a flow meter such as a heated wire mass flow meter. Due to the sensitivity with which the flow output must be measured, accurate measurement of the flow output is dependent upon the bias valve to provide at least one of inertial damping and viscous damping. Inertial damping provided by the bias valve is a result of the mass of a poppet which is slideably reciprocative within a cylinder.

Viscous damping is provided by the poppet as it reciprocates within the cylinder. More specifically, an annular poppet clearance located between the poppet and the cylinder results in the creation of the viscous damping which occurs when gas trapped at the bottom of the cylinder passes through the poppet clearance as the poppet moves downward into the cylinder. Conversely, gas must pass through the poppet clearance in reverse direction in order to fill the expanding volume at the bottom of the cylinder as the poppet moves out of the cylinder. The passage of the gas through the poppet clearance creates the viscous damping effect. Advantageously, the combined effects of the viscous and inertial damping are preferably sufficient to attenuate the pulsating flow output produced by the ROOTS® blower such that the flow meter may accurately measure flow output therefrom.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 2 is an exploded perspective view of the bias valve illustrating the interconnective relationship of individual components thereof;

FIG. 3 is a cross-sectional side view of the bias valve illustrating a poppet reciprocatively disposed within a cylinder.

DETAILED DESCRIPTION

Figure 1:
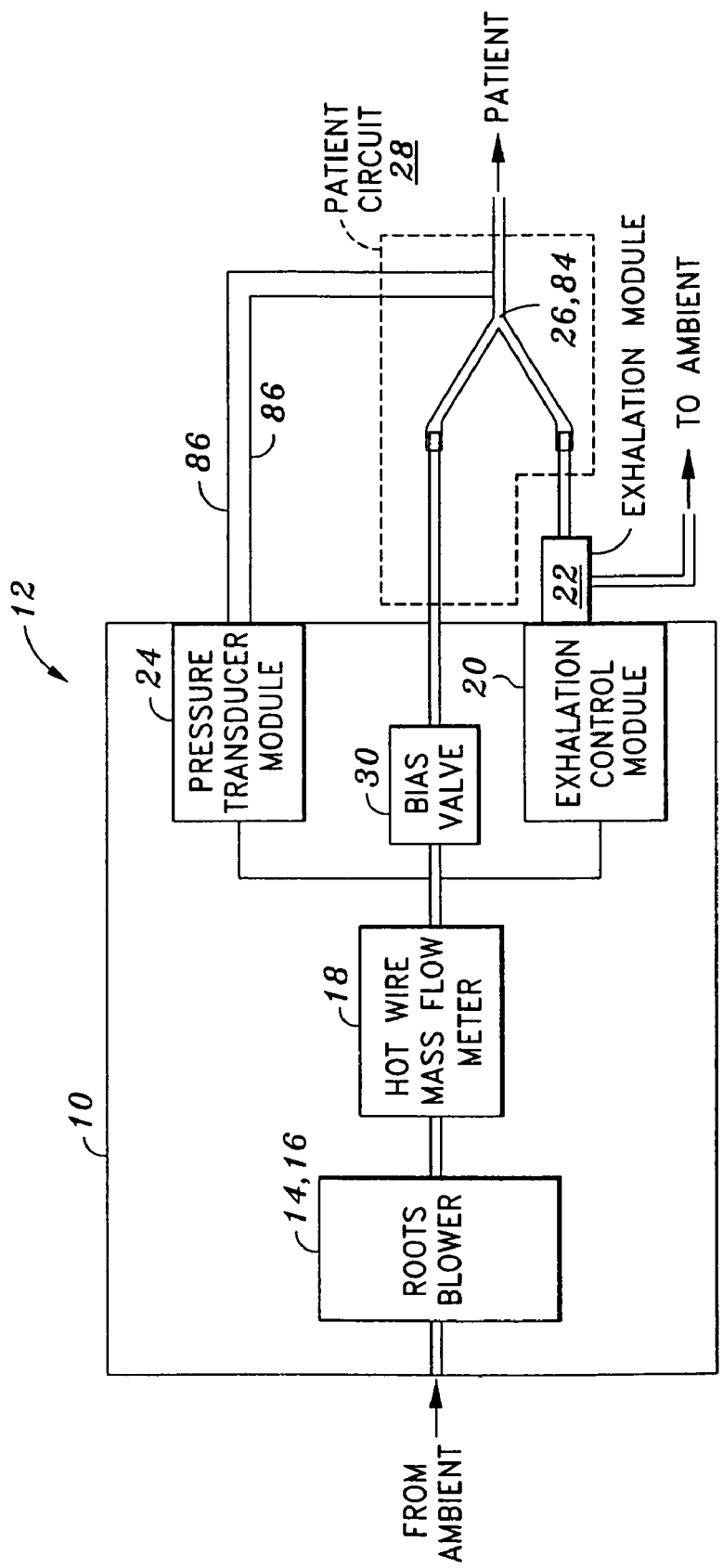
FIG. 1 is a pneumatic diagram of a ventilation system having a mechanical ventilator incorporating a ROOTS® blower and which may include an exhalation valve and an exhalation control module operative to close the exhalation valve during the breathing cycle and further illustrating a bias valve located downstream of the ROOTS® blower and being configured to facilitate accurate flow measurement by a flow meter and produce a bias pressure to facilitate operation of the exhalation control module.

Referring now to the drawings wherein the showings are for purposes of illustrating the present invention and not for purposes of limiting the same, shown is a portable mechanical ventilator 10 having a blower assembly 14 such as a ROOTS® blower 16 for producing gas flow to a patient or patient circuit 28 via a patient connection 26. As is described in greater detail in U.S. Patent Publication No. 2005/0051168 entitled PORTABLE VENTILATOR SYSTEM to DeVries et al., the entire contents of which is expressly incorporated by reference herein, the portable ventilator 10 operates in variable speed mode as the breath delivery mechanism and has improved efficiency and reduced size resulting from the use of the ROOTS® blower 16.

The portable mechanical ventilator 10 preferably includes sound-reducing elements to facilitate operation thereof in noise-sensitive environments such as in a patient-recovery room of a hospital. Furthermore, the portable mechanical ventilator 10 has reduced weight and reduced power consumption as compared to conventional mechanical ventilators. The above-noted advantages collectively contribute toward the portability aspects of the mechanical ventilator and therefore provides mobility to patients requiring continuous breathing assistance in remote locations, during patient transfers or during emergency situations such as power outages.

As is described in U.S. Patent Publication No. 20050051168, the portable ventilator 10 may include a docking cradle and a monitor wherein the docking cradle may support the portable ventilator 10 on a moveable stand. The docking cradle may further its own power supply or power source and/or recharging system in order to expand the portable ventilator 10 interface capabilities. The monitor may be a graphics display monitor which may be releasably mountable to the docking cradle in order to provide enhanced display capabilities.

Referring now to FIG. 1, shown is a pneumatic diagram of a ventilator system 12 illustrating the mechanical ventilator 10 and which includes a mass flow meter 18 located downstream of the ROOTS® blower 16. The ROOTS® blower 16 draws room air into an inlet filter and delivers pressurized gas to the patient. The flow meter 18 is adapted to measure gas flow produced by the ROOTS® blower 16.

Importantly, the mechanical ventilator 10 includes a bias valve 30 located downstream of the ROOTS® blower 16 between the flow meter 18 and the patient circuit 28. The bias valve 30 dampens the pulsating gas flow produced by the ROOTS® blower 16 in order to improve the accuracy of gas flow measurements taken by the flow meter 18. Although located downstream of the ROOTS® blower 16, the bias valve 30 is effective in dampening pulsations upstream of the bias valve 30 (i.e., at the flow meter 18) due to confinement of the gas flow within an air column or passageway extending between the ROOTS® blower 16 outlet and the bias valve 30. More specifically, the dampening effect of the bias valve 30 is transmitted upstream through the passageway to the flow emanating at the ROOTS® blower 16 outlet. Therefore, the flow received at the flow meter 18 is also dampened which allows the flow meter 18 to accurately measure gas flow output produced by the ROOTS® blower 16.

As can be seen in FIG. 1, the pneumatic diagram further includes an exhalation control module 20 which is operative to regulate the exhalation valve 22 that is connected to an exhalation limb of the patient circuit 28. The exhalation control module 20 is fluidly connected to the bias valve 30 which provides a bias pressure to facilitate operation of the exhalation control module 20 in closing the exhalation valve 22 during the inspiration phase. The pneumatic diagram also includes a pressure transducer module 24 which receives input from airway and flow sense lines 86 connected to the patient circuit 28. The pressure transducer module 24 is also fluidly connected to the bias valve 30 which provides a bias pressure to assist in purging the sense lines 86.

Optionally, the portable mechanical ventilator 10 may be configured such that compressed air that is not used by the patient during the exhalation phase may be recycled or recirculated. Furthermore, the portable mechanical ventilator 10 may be configured to deliver blended gas using an internal $O_2$ blender which may be monitored via an $FIO_2$ (fraction of inspired oxygen) sensor. $FIO_2$ may be displayed on a user interface along with the display of other operating parameters of the mechanical ventilator 10. As was earlier mentioned, the pneumatic circuit may further include the airway and flow sense lines 86 connected to the wye 84 junction in the patient circuit 28 to provide airway and flow values to the pressure transducer module 24 for use in a control loop for the mechanical ventilator 10.

Referring now to FIG. 2, shown is an exploded view of the bias valve 30 illustrating the interconnective relationship of the individual components thereof. As was earlier mentioned, the bias valve 30 is specifically configured to dampen the pulsating flow output of the ROOTS® blower 16 in order to improve the accuracy of the flow meter 18 and to provide a bias pressure to the exhalation control module 20 in order to improve the regulation of various breathing functions. The bias pressure is defined as an elevated drive pressure relative to patient circuit 28 pressure and is used by the exhalation control module 20 to perform a number of functions including, but not limited to, closing the exhalation valve 22 at the start of inspiration, regulating positive end expiratory pressure (PEEP) during exhalation, and purging the sense lines 86 (e.g., airway and flow lines) which extend from the wye 84 junction to the pressure transducer module 24. Purging of the sense lines 86 is periodically necessary as the sense lines 86 may become clogged or obstructed by moisture from patient's breath which may compromise the accuracy of flow and pressure measurements.

Referring to FIGS. 2-3, the bias valve 30, in its broadest sense, may comprise a valve seat 58, a poppet 64, and a biasing member 76 configured to bias the poppet 64 against the valve seat 58. As shown in FIG. 1, the bias valve 30 is fluidly connected to the ROOTS® blower 16 and receives gas flow therefrom at the valve seat 58. The poppet 64 is directly engageable to the valve seat 58 and is reciprocated between closed and open positions based on the amount of gas flow from the ROOTS® blower 16 to the patient circuit 28. The biasing member 76 produces a spring preload which biases the poppet 64 against the valve seat 58 to create the desired bias pressure at the exhalation control module 20 and at the pressure transducer module 24.

As was earlier mentioned, the bias pressure facilitates the operation of the exhalation control module 20 and pressure transducer module 24 which, in turn, allows for closing of the exhalation valve 22, regulation of PEEP, and purging of sense lines 86. In addition, the bias pressure aids in performance of user-activated maneuvers such as inspiratory-hold, expiratory-hold and regulation of mean inspiratory pressure/negative inspiratory force (MIP/NIF). More specifically, the bias valve 30 operates in conjunction with a blower control algorithm which controls the operation of the ROOTS® blower 16. The bias valve 30 and blower control algorithm collectively regulate flow into and out of the patient circuit 28 during the performance of user-activated maneuvers. The bias valve 30 does so by generating a slight bias pressure over the patient circuit 28 pressure in order to keep the exhalation valve 22 closed at the appropriate times.

During the inspiratory hold maneuver, the bias pressure is such that the exhalation valve 22 remains closed for a period of time during which certain measurements may be taken. In addition, inspiratory hold provides an additional period of time during which air may be maintained in the lungs allowing for more gas exchange to occur. The mechanical ventilator 10 may be pre-set to exit the inspiratory hold maneuver such as in the event of high airway pressure or a fault in the patient circuit 28. Following completion of the inspiratory hold maneuver, the exhalation valve 22 is opened to allow initiation of the exhalation phase of the breathing cycle.

During the expiratory hold maneuver, patient exhalation proceeds with the exhalation valve 22 in the open position to allow normal bias flow. However, the mechanical ventilator 10 may be configured to exit the expiratory hold maneuver upon the occurrence of certain events. For example, if patient breathing effort is detected during this maneuver, the mechanical ventilator 10 is preferably operative to exit the expiratory hold and deliver a breath to the patient. Upon completion of the expiratory hold maneuver, the exhalation valve 22 closes to allow initiation of the inspiration phase.

The bias valve 30 assists in the regulation of MIP/NIF by maintaining the exhalation valve 22 in the closed position to prevent forward flow into the patient circuit 28 which would otherwise jeopardize the accuracy of various pressure measurements. The MIP/NIF maneuver allows for determining the patient's readiness for weaning off the mechanical ventilator 10 by measuring the patient's ability to draw negative pressure within the closed patient circuit 28 in addition to measuring the airway pressure during this maneuver.

In each of the above user-activated maneuvers, the bias pressure maintains the exhalation valve 22 in the closed position to prevent any flow into or out of the patient circuit 28 for the duration of the maneuvers. The bias valve 30 performs this function by providing to the exhalation control module 20 a bias pressure (i.e., an elevated pressure relative to the patient circuit pressure) to the ventilator side of the patient circuit 28 in the ventilation system 12 illustrated in FIG. 1. In this regard, the bias valve 30 is preferably configured to provide a bias pressure of about 2 to 4 cm $H_2O$ above the patient circuit pressure.

The bias valve 30 is specifically adapted to provide this bias pressure due to the spring preload of the biasing member 76 to bias the poppet 64 against the valve seat 58, as will be described in greater detail below. In addition, the poppet 64 and valve seat 58 are specifically configured to provide a relatively tight or leak proof seal at the poppet/valve seat interface such that forward flow does not enter the patient circuit 28 in response to forward pressure acting upon the poppet 64. Preferably, the bias valve 30 is adapted to generate a bias pressure of 4 cm $H_2O$ at and allow for flow rates of up to 4 liters per minute (LPM) at only a few cm's of $H_2O$ above the 4 cm $H_2O$ bias pressure.

As can be seen in FIGS. 2-3, the biasing member 76 may be configured as a coil spring 78 which preferably has a spring constant that is sufficient to bias the poppet 64 against the valve seat 58 such that the bias pressure is substantially constant across a flow range of the ROOTS® blower 16. The bias pressure may be set at about 2-4 cm of $H_2O$ although other bias pressures may be utilized depending on system requirements. Advantageously, the ability to maintain the bias pressure relatively constant across the flow range of the ROOTS® blower 16 minimizes power consumption of the mechanical ventilator 10 while allowing the ROOTS® blower 16 to achieve its peak flow requirement.

A preferred structural arrangement of the bias valve 30 is shown in FIGS. 2-3 which illustrates a cylinder 46 having the poppet 64 reciprocative therewithin and further including the biasing member 76 which biases the poppet 64 toward its closed position. The bias valve 30 is comprised of a housing such as an elbow housing 40, a hollow cylinder 46 fixedly mounted within the elbow housing 40, and an annular valve seat 58 which receives gas flow from the ROOTS® blower 16. The elbow housing 40 and cylinder 46 collectively define an annular housing chamber 34.

The poppet 64 is reciprocative within the cylinder 46 along a valve axis 66. The cylinder 46 has a cylinder sidewall 50 and a cylinder end wall 48. A cylinder chamber 52 is defined between the cylinder end wall 48 and one of the poppet ends 70. The biasing member 76 may be configured as a coil spring 78 disposed within the cylinder chamber 52 and biases the poppet 64 against the valve seat 58. The housing inlet 38 receives flow from the ROOTS® blower 16 at the valve seat 58.

As was earlier mentioned, for power consumption purposes, it is beneficial to keep the bias pressure constant across the flow range of the ROOTS® blower 16. As such, the poppet 64 is specifically configured to be slideable within the cylinder 46 such that the poppet 64 may travel freely away from the valve seat 58 as flow from the ROOTS® blower 16 increases. In addition, the biasing member 76 preferably has a low spring constant which, combined with the free poppet 64 travel, allows the bias pressure to exhibit the preferred constant pressure characteristic over the flow range of the ROOTS® blower 16. The amount of spring preload and the amount of exposed area of the poppet 64 (i.e., seat area 72) when it is engaged to the valve seat 58 determines the amount of resistance (i.e., bias pressure) that is generated.

As shown in FIGS. 2 and 3, the elbow housing 40 has a housing sidewall 42 and a housing end wall 44 with the housing inlet 38 being formed on an end of the elbow housing 40 opposite the housing end wall 44 and being connected to the ROOTS® blower 16 at the valve seat 58. A housing outlet 36 is formed on the housing sidewall 42 and is fluidly connected to the patient circuit 28. As was earlier mentioned, the hollow cylinder 46 is fixedly mounted within the elbow housing 40 and is defined by a cylinder end wall 48 and a cylinder sidewall 50. The cylinder sidewall 50 is disposed in spaced coaxial relation to the housing sidewall 42 to define the annular housing chamber 34 therebetween.

The cylinder 46 is open on an end coincident with the housing inlet 38 (i.e., at the valve seat 58). The cylinder sidewall 50 has at least one radial opening 54 formed therein which acts to fluidly interconnect the housing inlet 38 to the annular housing chamber 34 and, ultimately, to the housing outlet 36. In one embodiment, the radial opening 54 may be comprised of a plurality of three equiangularly-spaced radial slots formed in the cylinder sidewall 50 at an upper portion thereof adjacent the valve seat 58.

The valve seat 58 is preferably configured as an annular element having a radial flange 60 fixedly mounted to the housing inlet 38. The valve seat 58 may further include an annular seat interface 62 which extends axially inwardly from the radial flange 60. The cylinder sidewall 50 may be fixedly contained within the elbow housing 40 by means of the valve seat 58. More specifically, in one embodiment, a portion of the cylinder sidewall 50 adjacent the valve seat 58 may be captured between the seat interface 62 and the elbow sidewall. Additionally or alternatively, the valve seat 58 may be press fit into the cylinder sidewall 50.

It should be noted that although the elbow housing 40 and cylinder 46 are shown and disclosed herein as being cylindrical, it is contemplated that the bias valve 30 may be configured in a variety of alternative shapes, sizes and configurations such as rectangular, oval and the like. The intended functions served by the bias valve 30 in dampening pulsating gas flow and providing bias pressure are dependent in part upon the mass of the poppet 64, the spring preload of the biasing member 76, and a seat area 72 of the poppet 64 against the valve seat 58. For purposes of generating the bias pressure, the poppet 64 may be configured in a variety of shapes such as a disc shape which is sealingly engageable against the valve seat 58 and which is reactive against the gas flow produced by the ROOTS® blower 16.

The poppet 64 itself may be cylindrically shaped and is preferably slideably disposable within the cylinder 46 along the valve axis 66. The poppet 64 has a cylindrical poppet side 68 surface and opposing poppet ends 70. A cylinder chamber 52 is formed between the cylinder end wall 48 and one of the poppet ends 70 with the other one of the poppet ends 70 being sealingly engageable against the seat interface 62 of the annular valve seat 58. As was earlier mentioned, when disposed against the valve seat 58, the poppet 64 defines the seat area 72 against which the pulsating gas flow from the ROOTS® blower 16 reacts.

Referring briefly to FIG. 1, the pneumatic diagram illustrates the flow meter 18 fluidly interconnecting the ROOTS® blower 16 to the bias valve 30. In a preferable embodiment, the flow meter 18 is configured as a heated wire mass flow meter 18 which, ideally, is configured to accurately measure flow produced by the ROOTS® blower 16. In order to improve the accuracy of the flow meter 18, the bias valve 30 is specifically configured to provide damping of the pulsating gas flow produced by the ROOTS® blower 16 at the heated wire mass flow meter 18. Advantageously, such damping is provided by at least one of inertial damping and viscous damping forces produced by the bias valve 30, as described in greater detail below.

Referring back to FIG. 2, the poppet 64 is sized and configured to be complementary to the cylinder 46. In this regard, the poppet side 68 and cylinder sidewall 50 define a substantially narrow annular poppet clearance 74 therebetween. The poppet clearance 74 is preferably sufficient to provide viscous damping of pulsating gas flow produced by the ROOTS® blower 16. Such viscous damping occurs when gas in the cylinder chamber 52 passes through the substantially narrow poppet clearance 74 and enters the housing chamber 34 via the radial openings 54 (i.e., radial slots) formed in the cylinder sidewall 50, and vice versa. The poppet 64 reciprocates in response to the pulsating gas flow acting against the seat area 72 of the poppet 64.

In addition, the poppet 64 preferably has a mass sufficient to provide inertial damping of the pulsating gas flow from the ROOTS® blower 16. Shown in FIG. 3 is a version of the poppet 64 which includes a counterbore formed therein for receipt of a mass element 80 secured to the poppet 64 via a pin 82 sealed with an O-ring 88. The biasing member 76 is shown configured as a coil spring 78 mounted within the cylinder chamber 52 and coaxially disposed over the mass element 80 within the counterbore in the poppet end 70. Variously-sized mass elements 80 may be substituted in order to increase or decrease the mass of the poppet 64 to achieve the desired inertial damping characteristics.

During operation of the ROOTS® blower 16, pulsating gas flow acts against the poppet 64 at a forcing frequency. The poppet 64 and biasing member 76 are reciprocative within a cylinder 46 at a poppet natural frequency due in part to the mass of the poppet 64/mass element 80 and the spring rate of the spring 78. The poppet 64 and mass element 80 are preferably sized and configured to maximize inertial damping of the pulsating gas flow when the forcing frequency is substantially higher than the poppet natural frequency. A high forcing frequency relative to poppet natural frequency is the typical relationship between the poppet/biasing member 64, 76 and ROOTS® blower 16 during a majority of the operation of the mechanical ventilator 10. Advantageously, inertial damping of the pulsating gas flow allows for increased accuracy of measurement by the heated wire mass flow meter 18 utilized in the preferred embodiment of the mechanical ventilator 10.

As was earlier mentioned, viscous damping is provided by the poppet clearance 74 between the poppet side 68 and the cylinder sidewall 50. As the poppet 64 moves inwardly toward the cylinder chamber 52 in response to the gas flow acting at the valve seat 58, gas contained within the cylinder chamber 52 is forced through the substantially narrow poppet clearance 74 whereupon it enters the housing chamber 34 via the radial openings 54. Likewise, as the poppet 64 moves away from the cylinder end wall 48, the gas reverses direction and travels from the housing chamber 34 through the poppet clearance 74 and fills the cylinder chamber 52.

Figure 4:
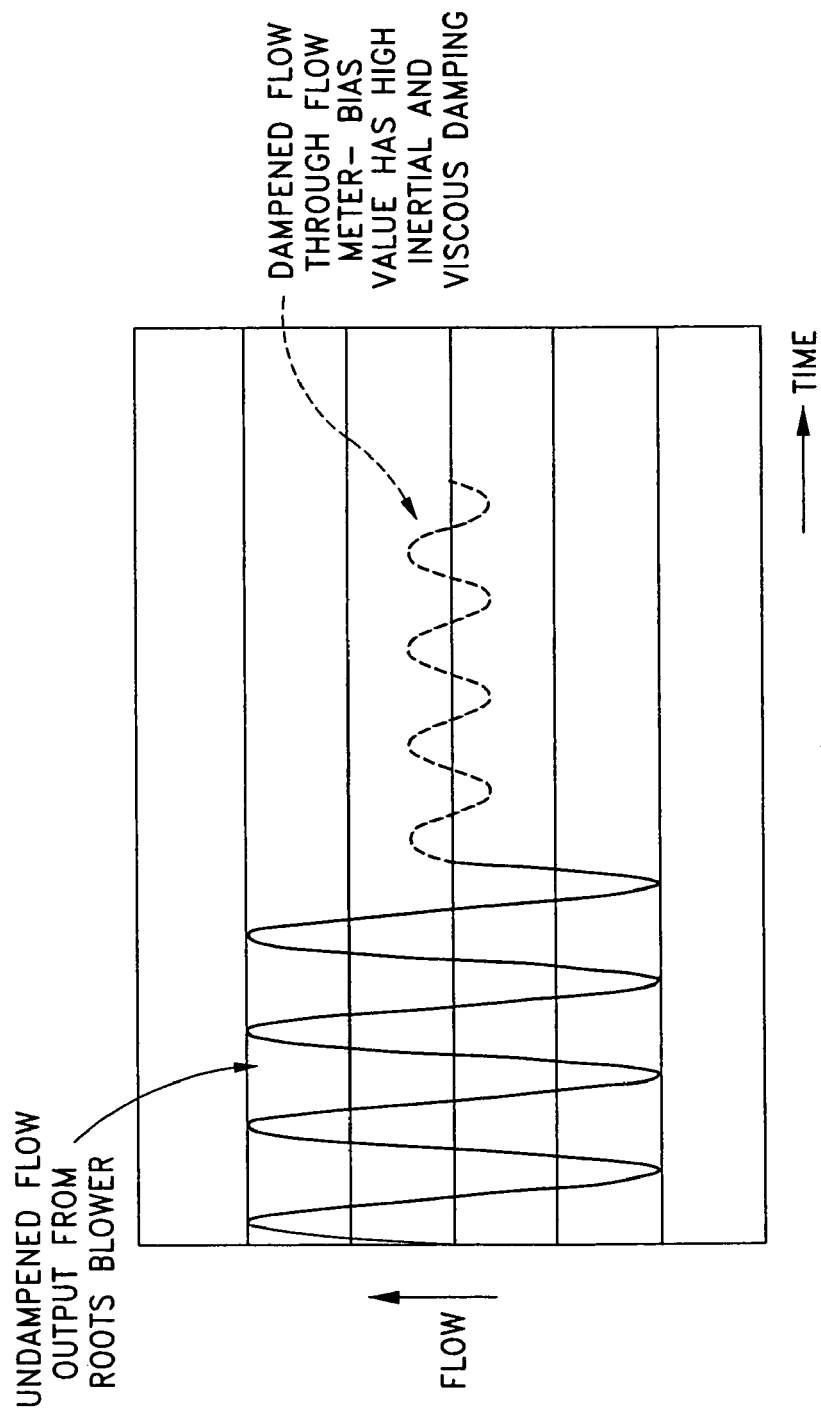
FIG. 4 is a graph illustrating on a left side thereof a high-amplitude undampened pulsating flow output of the ROOTS® blower and, on the right side of the graph, a relatively low amplitude of dampened flow of the ROOTS® blower as a result of inertial damping and viscous damping generated by the bias valve.

The viscous damping occurring as a result of the gas traveling through the poppet clearance 74 is most effective when the forcing frequency acting upon the poppet 64 is substantially equal to the poppet natural frequency. An example of the damping effects of the bias valve 30 is visible in the graph of FIG. 4 which, on the left side, illustrates the flow output from the ROOTS® blower 16 in an undampened state. On the right side of the graph is a plot of the attenuated or damped flow output from the ROOTS® blower 16. The dampened flow is a result of inertial and viscous damping generated by the bias valve 30.

Referring back to FIGS. 2-3, regarding specific structural configurations for various components of the bias valve 30, it is contemplated that the cylinder 46 is fabricated of a suitable metallic material such as stainless steel although any suitable material may be used. Due to the relatively close fit required between the poppet 64 and the cylinder 46, the cylinder sidewall 50 inner surfaces may be fabricated at tight tolerances by a variety of means including machining such as CNC machining. Unfortunately, such machining processes may result in turning marks formed on the cylinder sidewall 50 which are oriented transversely to the direction of reciprocation of the poppet 64. Due to the need for high cycle-life of the poppet 64 (i.e., as a result of poppet 64 reciprocation), the inner surface of the cylinder sidewall 50 is preferably smoothed or burnished in order to reduce surface roughness and provide a smooth surface with minimal resistance to the poppet 64 movement.

In this same regard, it is contemplated that the poppet 64 itself is preferably fabricated of a material exhibiting low friction characteristics and favorable mechanical properties as well as a low coefficient of thermal expansion in order to avoid size variations in the poppet clearance 74. For these reasons, the poppet 64 is preferably fabricated of a synthetic polymer such as polyetheretherketone (PEEK) which is known to have high tensile strength and high lubricity. The valve seat 58 is preferably fabricated of brass due to its favorable mechanical properties including high hardness and favorable workability characteristics although the valve seat 58 may be fabricated of any suitable material. The biasing member 76, which may be configured as a coil spring 78, may also be preferably fabricated of spring steel or stainless steel although any suitable material may be utilized.

In operation, the ROOTS® blower 16 produces a pulsating gas flow which is delivered to the bias valve 30 as illustrated in the pneumatic diagram of FIG. 1. Due to the configuration of the poppet's engagement to the valve seat 58, the bias valve 30 generates the bias pressure which is an elevated drive pressure relative to the patient circuit 28 pressure. As was earlier mentioned, such drive pressure is utilized by the exhalation control module 20 in order to close the exhalation valve 22 at the start of inspiration, regulate PEEP during exhalation, and which the pressure transducer module 24 uses to purge the sense lines 86 connected at the wye 84 adjacent to the patient circuit 28.

The bias pressure is generated due to the biasing member 76 spring preload responding to the pulsating flow acting upon the seat area 72 of the poppet 64. The biasing member 76 is sized and configured to provide a predetermined spring preload which, in turn, results in a desired amount of bias pressure above the patient circuit 28 pressure. Preferably, the biasing member 76 has a relatively low spring constant such that the bias pressure is substantially constant across the flow range of the ROOTS® blower 16. The bias pressure is preferably high enough to aid the exhalation control module 20 in performing the above-mentioned functions as well as aiding in user-activated maneuvers such as inspiratory-hold and expiratory-hold.

Advantageously, the unique arrangement of the bias valve 30 also provides damping of the pulsating gas flow produced by the ROOTS® blower 16 such that the flow meter 18 that is fluidly connected to the ROOTS® blower 16 may accurately measure flow produced thereby. The damping generated by the poppet 64 may be a result of at least one of inertial damping and viscous damping. As was earlier mentioned, the inertial damping is dependent upon the poppet 64 mass in combination with reactive force produced by the biasing member 76.

The amount of viscous damping is dependent upon the size of the poppet clearance 74 between the poppet 64 and cylinder 46 as the poppet 64 reciprocates therewithin. Ideally, the poppet 64 and mass element 80 are sized and configured to maximize inertial damping when the forcing frequency (i.e., produced by the pulsating gas flow acting upon the poppet 64) is substantially higher than the poppet natural frequency. In addition, the bias valve 30 is preferably configured to maximize viscous damping when the forcing frequency is substantially equal to the poppet natural frequency. The combined effects of the viscous and inertial damping are preferably sufficient to enhance the accuracy with which the flow meter 18 measures flow produced by the ROOTS® blower 16.

The description of the various embodiments of the present invention are presented to illustrate preferred embodiments thereof and other inventive concepts may be otherwise variously embodied and employed. The appended claims are intended to be construed to include such variations except insofar as limited by the prior art.

What is claimed is:

1. A bias valve apparatus for attenuating pulsating gas flow from a gas source to a flow-receiving device, the bias valve apparatus comprising:
    a housing assembly, comprising:
        an annular housing chamber opening to a housing outlet fluidly connected to the flow-receiving device and to a housing inlet fluidly connected to the gas source; and
        a housing having a housing sidewall and a housing end wall, the housing inlet being formed on an end opposite the housing end wall, the housing outlet being formed on the housing sidewall;
        a hollow cylinder fixedly mounted within the housing assembly and having a cylinder end wall and a cylinder sidewall, the cylinder sidewall being disposed in spaced coaxial relation to the housing sidewall to define the housing chamber therebetween, the cylinder being open on an end coincident with the housing inlet; and
        an annular valve seat fixedly mounted to the housing inlet and having a seat interface; a poppet slidably disposed within the cylinder and reciprocatively moveable therewithin,
    wherein:
        the poppet includes a poppet side and opposing poppet ends;
        a cylinder chamber is defined between the cylinder end wall and one of the poppetends, and
        the other one of the poppet ends is configured to be sealingly engageable to the seat interface and defining a seat area; and
        a spring having a spring preload sufficient to bias the poppet toward the seat interface; and
    wherein the bias valve apparatus is used in conjunction with a ventilator having an exhalation control module fluidly connected to the bias valve apparatus;
    wherein the gas source includes a Roots-type blower assembly and the flow-receiving device includes a patient circuit fluidly connected to an opposite side of the bias valve apparatus, and
    wherein the exhalation control module is configured to operate an exhalation valve connected to the patient circuit.

2. The bias valve apparatus of claim 1, further comprising:
    a mass flow meter interposed between the gas source and the bias valve apparatus;
    wherein the mass flow meter is configured to measure gas flow from the gas source.

3. The bias valve apparatus of claim 1, wherein the flow-receiving device includes a patient circuit.

4. The bias valve apparatus of claim 1, wherein the seat area and spring preload are sized and configured to provide a predetermined bias pressure at the exhalation control module.

5. The bias valve apparatus of claim 1, wherein the poppet has a mass sufficient to generate inertial damping of the pulsating gas flow.

6. The bias valve apparatus of claim 1, further comprising:
    a mass element attached to the poppet,
    wherein:
        the poppet reacts against the pulsating gas flow at a forcing frequency;
        the poppet and spring are reciprocative at a poppet natural frequency, and
        the poppet and mass element are sized and configured to provide a highest degree of inertial damping when the forcing frequency is substantially higher than the poppet natural frequency.

7. The bias valve apparatus of claim 6, wherein the bias valve is configured to provide a highest degree of viscous damping of the pulsating gas flow when the forcing frequency is substantially equal to the poppet natural frequency.

8. The bias valve apparatus of claim 1, wherein the poppet and cylinder define a substantially narrow poppet clearance therebetween for generating viscous damping that occurs when gas passes through the poppet clearance between the cylinder chamber and the housing chamber during poppet reciprocation.

9. The bias valve apparatus of claim 1, wherein the spring has a spring constant sufficient to generate a substantially constant bias pressure across a flow range of the blower assembly.

10. A ventilator, comprising:
    a blower assembly for producing a gas flow;
    an exhalation control module;
    a patient circuit, the exhalation control module being configured to operate an exhalation valve connected to the patient circuit;
    a bias valve comprising:
    a housing assembly comprising:
    an annular housing chamber that forms a housing outlet fluidly connected to the patient circuit and a housing inlet fluidly connected to the blower assembly;
    a housing comprising:
    a housing sidewall; and
    a housing end wall,
    wherein the housing inlet is formed on an end of the housing assembly opposite the housing end wall and is connected to the blower assembly, and
        wherein the housing outlet is formed on the housing sidewall; a hollow cylinder fixedly mounted within the housing assembly and comprising: a cylinder end wall; and a cylinder sidewall,
        wherein the cylinder sidewall is disposed in spaced coaxial relation to the housing sidewall to define the housing chamber therebetween, and
        wherein the cylinder is open on an end coincident with the housing inlet; and
            an annular valve seat fixedly mounted to the housing inlet and having a seat interface;
            a poppet slidably disposed within the cylinder and reciprocatively moveable therewithin and comprising:
            a poppet side; and
            opposing poppet ends,
            wherein a cylinder chamber is defined between the cylinder end wall and one of the poppet ends, and
            wherein the other one of the poppet ends is configured to be sealingly engageable to the seat interface to define a seat area; and
            a biasing member having a spring preload sufficient to bias the poppet toward the seat interface,
            wherein the exhalation control module is fluidly connected to the bias valve and the patient circuit is fluidly connected to an opposite side thereof.

* * * * *